United States Patent [19]
Machino et al.

[11] Patent Number: 6,048,733
[45] Date of Patent: Apr. 11, 2000

[54] DMS DETECTING AGENT, METHOD FOR PREPARING THE SAME AND DMS DETECTOR TUBE

[75] Inventors: Akira Machino, Ichikawa; Ikuno Uchida, Kodaira; Takanori Yoshimori; Kunitoshi Matsunobu, both of Yokohama, all of Japan

[73] Assignees: Tokyo Gas Co., Ltd., Tokyo; Gastec Corporation, Ayase, both of Japan

[21] Appl. No.: 09/060,967

[22] Filed: Apr. 15, 1998

[30] Foreign Application Priority Data

Jun. 27, 1997 [JP] Japan ..................... 9-187584

[51] Int. Cl.$^7$ .................................. G01N 21/75
[52] U.S. Cl. .................. 436/166; 436/120; 436/167; 422/85; 422/86; 422/88
[58] Field of Search ................ 436/56, 119, 120, 436/166, 167; 422/85, 86, 88

[56] References Cited

U.S. PATENT DOCUMENTS

| | | |
|---|---|---|
| 4,225,417 | 9/1980 | Nelson . |
| 4,268,440 | 5/1981 | Werther et al. ............ 260/393.3 |
| 4,277,368 | 7/1981 | Amy et al. . |
| 4,421,719 | 12/1983 | Burleigh ..................... 422/57 |

FOREIGN PATENT DOCUMENTS

| | | |
|---|---|---|
| 0 577 263 A1 | 1/1994 | European Pat. Off. . |
| XP-2083912 | 11/1996 | Japan . |
| XP-2083913 | 3/1997 | Japan . |
| XP-2083911 | 10/1997 | Japan . |
| XP-2083910 | 11/1997 | Japan . |
| 2 291 055 | 1/1996 | United Kingdom . |

OTHER PUBLICATIONS

Drager, "Detector Tube Handbook", 4th ed, p. 72, Aug. 1979.

Oxidative Control of Organosulfur Pollutants, 1979 American Chemical Society, vol. 13, No. 11, David C. Ayres and Catherine M. Scott, p. 1383.

*Primary Examiner*—Lyle A. Alexander
*Attorney, Agent, or Firm*—Flynn, Thiel, Boutell & Tanis, P.C.

[57] ABSTRACT

A DMS detecting agent with a permanganate deposited on a support, characterized in that the support is quartz sand, and that the DMS detecting agent is obtained by adding an aqueous solution of silica sol or alumina sol and a permanganate to said quartz sand support for mixing and then drying the mixture, and a DMS detecting agent tube and a DMS detector tube using the same.

8 Claims, 4 Drawing Sheets

○: SAMPLE GAS WITH DMS ADDED TO TBM OF 2.5vol ppm

●: SAMPLE GAS CONTAINING ONLY DMS

▲: DRY AIR CONTAINING DMS OF 4.5vol ppm

●: DRY AIR CONTAINING DMS OF 0.8vol ppm

TEMPERATURE / K
†CORRECTION FACTOR = 1.0 AT 293K

DMS DETECTING AGENT, METHOD FOR PREPARING THE SAME AND DMS DETECTOR TUBE

BACKGROUND OF THE INVENTION

1. Field of the Invention

The present invention relates to a detecting agent for measuring dimethyl sulfide (DMS: $H_3C-S-CH_3$, referred to as "DMS" in the present specification) contained in a fuel gas such as city gas and LP gas as an odorant or generating at a manufacturing factory and life environment easily, rapidly and precisely, and a method for preparing the same. Additionally, the present invention relates to a detecting agent tube for DMS in a gas-phase.

2. Prior Arts

City gas, LP gas and other fuel gases to be sent from a source of supply to each home by means of a pipe are sent to various combustion appliances such as a boiler burner, a gas turbine or a gas engine, a gas heater, a gas range, a gas rice cooker, an instantaneous water heater, a bath boiler and a gas stove through a pressure adjuster, a gas meter, an on-off valve and other various appliances provided on each pipe and consumed.

No matter whether they are in use or not, these fuel gases must always be kept from leaking from these pipes, various appliances and various combustion appliances. In addition, sufficient care must be taken in order to avoid danger due to imperfect combustion in various combustion appliances.

The leakage of a gas may occur not only from pipes, joints, gas meters and valves but also from various combustion appliances themselves. Hence, the leakage of a gas is observed by detecting a gas flow and measuring the flow rate, and necessary repair and control are performed on the pipe chase and gas appliances to maintain safety according to the results of the observation. One of the techniques for detecting the leakage of a gas immediately and giving warning of danger is a method of sensing leakage easily and immediately by adding an odorous compound such as mercaptan into a fuel gas.

As such an additive an odorous compound, namely, an odorant, generally, a sulfur compound such as tetrahydrothiophene (THT:$C_4H_8S$), tert-butyl mercaptan [TBM: $C(CH_3)_3-SH$] and DMS are employed singly or as an admixture of two or more components.

Looking at the condition of the use thereof in our country, THT is the most used, and TBM-based ones are secondarily used the secondly most. However, if it is restricted to enterprises supplying city gas with LNG as a main raw material, most of them employ a mixed odorant of TBM and DMS.

In order to measure the amount of an odorant, generally a gas chromatograph equipped with a flame photometric detector (FPD-GC method) is employed at a laboratory level. However, since the leakage of a gas occurs not only from pipe lines, joints, gas meters and valves but also from various combustion appliances themselves, the method for mesuring the odorant, rapidly and precisely in the field is keenly desired.

In this connection, in the case of the odorant being TBM, a practical use has already been realized. In the case of the odorant being THT, there exists (1) a transferable gas chromatograph [J. High Resolut. Chromatogr., 16, 379 (1993)], (2) a THT measuring machine and (3) a THT detector tube (Dräger, Germany), each have its merits and demerits.

In particular, the above conventional (3) THT detector tubes require much time for measurement and besides show unclear coloring, a large readout error and insufficient results of measurement, and there exists no proper one. The present inventors have solved various problems in conventional detecting agents and have developed a THT detecting agent capable of obtaining a detecting agent exhibiting clear coloring over a short time elaborately and a THT detector tube employing the same (Japanese Patent Application No. 8-262530).

An odorant in city gas is one of the important items in the control of quality, and it needs be contained in an amount enabling the object of addition, namely, the object of warning of leakage, to be accomplished, and the presence and amount of the odorant must always be observed. Because of this, the number of traders concerned with measuring the concentration also at the end of a gas pipe line is increasing. In this connection, regarding TBM and THT, a detector tube capable of measuring the concentration at the field of the end of a gas pipe line easily has already been developed, but there exists none for DMS.

It is known that sulfides such as DMS are oxidized by potassium permanganate to produce sulfone. The present inventors manufactured as an experiment various DMS detecting agent tubes with a permanganate as a detecting reagent and examined the characteristics thereof in detail, and as a result, have found that a detecting agent obtainable by selecting quartz sand particularly as a support and depositing potassium permanganate on the quartz sand is highly sensitive to DMS in city gas. It has become apparent that, in the case of depositing only potassium permanganate on quartz sand, however, the coloring is unclear, the readout error is large and the results of measurement are insufficient. The present invention has led, on the basis of this knowledge, to the development of a detecting agent capable of measuring DMS simply, rapidly and precisely, a process for preparing the same and a detecting agent tube for DMS in a gas phase.

SUMMARY OF THE INVENTION

It is the object of the present invention to provide an excellent detecting agent for measuring the presence or amount of DMS added to fuel gases such as city gas and LP gas as an odorant or the presence or amount of DMS generated at a manufacturing factory and life environment and a method for preparing the same, and also to provide a DMS detecting agent tube employing the detecting agent capable of performing the measurement simply, rapidly and precisely and showing an extremely small readout error and a DMS detector tube. In the present specification, a DMS detecting agent tube having a pretreatment tube is referred to as a DMS detector tube.

The present invention provides (A) a DMS detecting agent with a permanganate deposited on a support, characterized in that the support is quartz sand, and that the DMS detecting agent is obtained by adding an aqueous solution of silica sol or alumina sol and a permanganate to said quartz sand support to mix and then drying the mixture.

That is, the present invention provides (A) a DMS detecting agent with a permanganate deposited on a support comprising; (1) quartz sand as a support, (2) silica gel or alumina gel, and (3) a permanganate, wherein silica gel or alumina gel and the permanganate are deposited on the support.

The present invention provides (B) a method for preparing a DMS detecting agent with a permanganate deposited on a support. Washing said quartz sand support with pure water, adding an aqueous solution of silica sol or alumina sol and a permanganate thereto to form a mixture and drying the mixture.

Moreover, the present invention provides (C) a DMS detecting agent tube, characterized in that said DMS detecting agent tube is charged with a DMS detecting agent obtained by adding an aqueous solution of silica sol or alumina sol and a permanganate to a quartz sand support to form a mixture and then drying the mixture.

Besides, the present invention provides (D) a detector tube for DMS in a fuel gas comprising a pretreatment tube and a DMS detecting agent tube, characterized in that said DMS detecting agent tube is a DMS detecting agent tube charged with a DMS detecting agent obtained by adding an aqueous solution of silica sol or alumina sol and a permanganate to a quartz sand support to form a mixture and then drying the mixture.

PREFERRED EMBODIMENTS OF THE INVENTION

A DMS detecting agent, a DMS detecting agent tube and a DMS detector tube according to the present invention detect the presence of DMS in fuel gases such as city gas and LP gas and DMS present at a DMS manufacturing factory, a factory having a possibility of generating DMS or the atmosphere due to various causes, and besides are employed for measuring the DMS concentration. The above permanganate is not restricted so far as it is a permanganate capable of impregnating and being deposited as an aqueous solution together with silica sol or alumina sol on a quartz sand support, preferably potassium permanganate being employed. Quartz sand is employed as a support. Quartz sand comprises quartz as a main component and exists in a form of a fine powder, a fine particle, a particle and the like and, in the present invention, quartz sand in any form can be employed.

In the present invention, it is indispensable to employ silica sol or alumina sol in depositing a permanganate on quartz sand, of them, silica sol is employed preferably. Hereunder, silica sol will be described mainly, but it is also true of alumina sol.

In a preferred embodiment of preparation (production) according to the present invention, quartz sand is washed fully, subsequently an aqueous solution of silica sol and a permanganate is mixed and stirred with the washed quartz sand support, and then the mixture is dried. Drying must be performed sufficiently, and, for this, vacuum drying is employed preferably. The silica sol is changed to silica gel with the drying.

Figure 1:
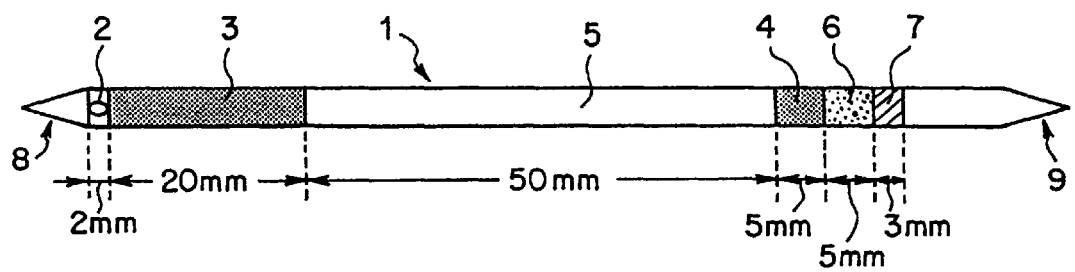
FIG. 1 is a diagram showing the outline of a DMS detecting agent tube charged with a DMS detecting agent according to the present invention.

FIG. 1 is a diagram showing the outline of a DMS detecting agent tube charged with the DMS detecting agent. In FIG. 1, mark 1 shows a detector tube. As a material for the tube 1, transparent plastic and glass can be used, and preferably, it is composed of a transparent and hollow glass tube. 2 shows a glass bead, 3 and 4 show isolating agents, and as isolating agents 3 and 4 can be used, for example, alumina or silica. 5 shows a layer charged with a detecting agent according to the present invention, 6 shows a protectant, and 7 shows a packing. Materials for the packing 7 are not particularly restricted so far as they have no influence upon the performance of the detecting agent, and, for example, polyethylene resins are used.

The protectant 6 is charged and provided in order to remove volatile components (mainly organic compounds) from the packing 7, and uses, for example, active alumina impregnated with an aqueous potassium permanganate solution. Both ends 8 and 9 of the detector tube 1 must be sealed airtightly before use. In the case that it is a hollow glass tube, sealing can be performed by performing heat fusion bonding after feeding the above agents, and both ends 8 and 9 are cut in use to open. The dimensions described in FIG. 1 show the approximate dimensions of the parts, and they are not restricted thereto and the same can be said about the dimensions shown in FIG. 2 to be described below.

In order to perform the detection of DMS in a gas by the above detecting agent tube rapidly, precisely and sharply, making the readout error as small as possible, obstructive gas components having bad influence upon the detection of DMS must be removed in advance. In the detection and measurement of DMS in a gas containing DMS singly, the DMS detector tube of the present invention is used without pretreatment (TBM detector tube). In this case, too, it goes without saying that a pretreatment tube for the removal of such obstructive gas components can be used on demand.

Figure 2:
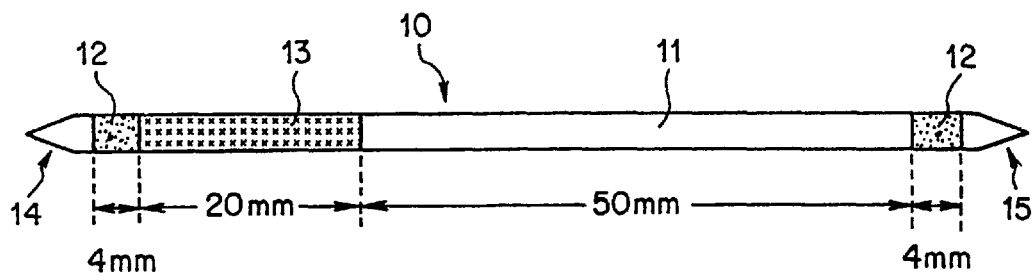
FIG. 2 is a diagram showing one example of a pretreatment (TBM detector tube) for removing obstructive gas components in a sample gas in advance.

In the case that a gas to be detected is a fuel gas, DMS is used generally together with TBM, however, a DMS detecting agent is discolored by TBM and hence, TBM must be removed in advance. FIG. 2 shows one example (10) of a pretreatment tube for this. This is a TBM detector tube but corresponds to a pretreatment tube. As materials for this tube can be used glass and plastic similarly as in the case of a detecting agent tube, and preferably it is composed of a hollow glass tube. In the case that, in measuring the presence and amount of DMS, a gas to be detected contains no TBM, the above pretreatment tube for TBM is not required. However, in order to perform the detection and measurement of DMS without errors, such a pretreatment tube for the removal of such obstructive gas components is used preferably.

In FIG. 2, 11 shows a TBM remover (TBM detecting agent), and 12 shows a packing. Materials for the packing 12 (two spots on right and left) are not particularly restricted so far as they have no influence upon the performance of said remover, and, for example, polyethylene resins are used and in the case of the present example, a second packing 13 like silica sand is charged. Both ends 14 and 15 of the pretreatment tube 10 must be sealed airtightly before use and in the case that it is a hollow glass tube, it is heat-fusion-bonded after charging a remover 11, and both ends 14 and 15 are cut in use to open.

Figure 3:
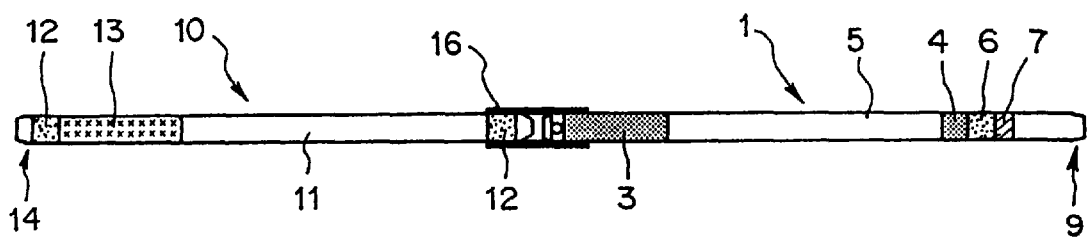
FIG. 3 is a diagram showing in the state which a DMS detecting agent tube connects in series with a pretreatment tube (TBM detector tube).

In the use of the DMS detecting agent tube 1 and the pretreatment tube 10, both ends of the detecting agent tube 1 and both ends of the pretreatment tube 10 are cut open, and the pretreatment tube 10 is connected to the front of the detecting agent tube 1. FIG. 3 shows the outline of the connection condition in a relatively reduced scale as compared with FIG. 1 and FIG. 2, and the same part is shown by the same numeral.

16 shows a connector between the left end part of the detecting agent tube 1 and the right end part of the pretreatment tube 10, which is composed of a rubber tube or the like. In use, the end part 14 of the pretreatment tube 10 is connected to a gas source like a gas to be detected, and at the same time a gas-collecting device is connected to the end part 9 of the detecting agent tube 1. When a gas to be detected is sucked from the gas-collecting device, the gas to be detected passes through the layer of the remover 11 to reach the layer 5 charged with the detecting agent and the presence and amount of DMS in the gas to be detected can be measured by observing the color layer change here.

Permanganate ions release oxygen (oxidize a substance), receiving a reduction action themselves, and perform a change represented by the following formula. The above color layer change is made by the reduction reaction of DMS by permanganate ions of a permanganate deposited on a quartz sand support according to the present invention when DMS is present or is contained in a prescribed amount or more, $MnO_4^-$ ions (red violet; near pink, combining with the white color of quartz sand of a support) are reduced to brown $Mn^{4+}$ ions in a short time like 60 seconds and change to clear yellow, mixing with the color of quartz sand of a support.

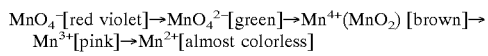

$MnO_4^-$[red violet]→$MnO_4^{2-}$[green]→$Mn^{4+}(MnO_2)$ [brown]→ $Mn^{3+}$[pink]→$Mn^{2+}$[almost colorless]

In the case of depositing only potassium permanganate on a quartz sand support, the color is also pink but is faded, and the coloring is indistinct. Because of this, if it is charged into a detector tube, the readout error is large. In contrast, the DMS detecting agent of the present invention using silica sol together with potassium permanganate also exhibits a pink color, but the coloring is remarkably distinct as compared with the case of depositing only a quartz sand, and the coloring difference at the boundary part of a color layer change in use (coloring difference at the boundary part of a discoloring part and a non-discoloring part) is also remarkably sharp. Thus, it has been revealed that both have a remarkable difference in distinctness.

Figure 6:
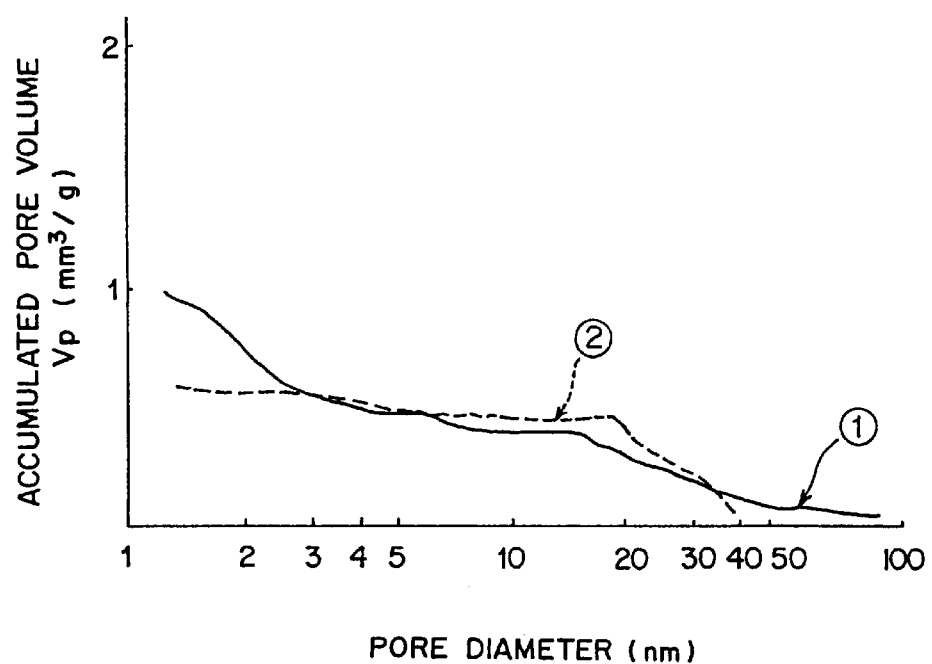
FIG. 6 is a diagram showing the pore distributions of the detecting agent and the detecting agent of a comparative example of the present invention.

Table 1 shows the amounts of deposition and the specific surface areas of two detecting agents of a detecting agent according to an example and a detecting agent according to comparative example to be described later, and FIG. 6 shows the pore distributions thereof. About 5 g of each detecting agent was vacuum-dried at 373 K for 5 hours and then the amount of nitrogen adsorption was measured, mono-layer molecular adsorption was supposed from this value to obtain the specific surface area and the pore volume thereof. As is apparent from Table 1 and FIG. 6, both detecting agents are the same in the amount of the deposition of potassium permanganate on quartz sand but are different in the specific surface area and the pore distribution. In addition, ① of FIG. 6 shows the detecting agent of example and ② of FIG. 6 shows the detecting agent of the comparative example. In the detecting agent ① of the example, pores of less than 2 nm increase and the specific surface area also increases by the addition of the silica sol. It is considered from this point that the increase of the ratio of pores of less than 2 nm is effective for the formation of the boundary between a discoloring part and a non-discoloring part in measurement.

TABLE 1

|  | Amount of deposition of $KMnO_4$ (m/g) | Specific surface area (m²/g) |
| --- | --- | --- |
| Example | 0.026 | 0.53 |
| Comp. Ex. | 0.026 | 0.47 |

As described above, it is indispensable for the preparation of the DMS detecting agent of the present invention (1) to use quartz sand as a support and (2) to use silica sol together in depositing a permanganate on quartz sand, and thereby excellent characteristics as a DMS detecting agent can be obtained. Of them, the role of silica sol in (2) is unclear, but, according to the results of observation by comparing this case with the case of using no silica sol, pores of, for example, less than 2 nm increase and the specific surface area also increases by the addition of silica sol. Reasons for the above excellent characteristics can be guessed from this point that the increase of the ratio of pores of, for example, less than 2 nm acts effectively for the formation of the boundary between a discoloring part and a non-discoloring part in measurement and plays an important role upon the characteristics.

In addition, in the preparation of the DMS detecting agent of the present invention, it is also desirable (3) to wash a quartz sand carrier with pure water fully, (4) to add an aqueous solution of silica sol and a permanganate to said quartz sand support to stir and mix fully, and (5) to dry the mixture fully. The excellent characteristics of the present DMS detecting agent are caused mainly by the above (1) and (2), and a DMS detecting agent having particularly excellent characteristics can be surely obtained by further taking the points (3) to (5) into consideration.

In the embodiment of the above (3), quartz sand is washed with pure water fully. "Being washed fully" here means that these supports are washed with pure water completely, and as pure water for washing and being contained can be used ion exchange water with a high purity and distilled water. In the present invention, as described above, a support is washed with pure water fully, subsequently an aqueous solution of silica sol and a permanganate is added to the washed quartz sand support and stir red and mixed fully, and then the mixture is dried fully.

As a sample gas-collecting device (gas-collecting device) can be used any of vacuum-type, lead-in-type and bellows-type gas-collecting devices.

Figure 4:
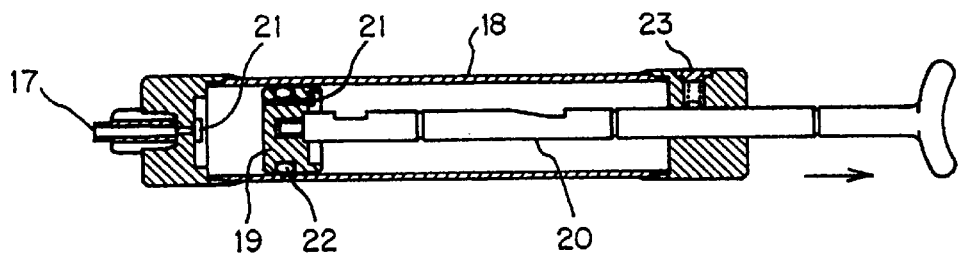
FIG. 4 is a diagram showing one example of a vacuum-type gas-collecting device.

FIG. 4 shows one example of a vacuum-type gas-collecting device. This is a method that the inside of the cylinder of the gas-collecting device connected to a DMS detecting agent tube or a DMS detector tube is made to be in a vacuum state by a piston and a sample gas is sucked through the detector tube. The detector tube is connected to the mounting opening 17 of the detector tube. In operation, a shaft 20 connected to a piston 19 is moved in the direction of the arrow to the cylinder 18 to make the inside of the cylinder 18 to be in a vacuum state, and a prescribed amount of the sample gas is introduced into the detector tube. In this case, a prescribed and constant amount of the sample gas can be introduced into the detector tube by setting up a gas volume corresponding to the width of the movement of the piston 18 in advance. In the drawing, 21 shows a non-return valve, 22 shows a packing, and 23 shows a stopper.

EXAMPLES

The present invention will now be described in more detail according to examples. Of course, the present invention is not restricted to these examples.

(Preparation of DMS Detecting Agent Tubes)

<Preparation of Detecting Agents>

Quartz sand (manufactured by Kyoritsu Yogyo Genryo Co., Ltd.; specific surface area: 950 $cm^2/cm^3$) was prepared, washed with an aqueous dilute nitric acid solution and then washed with 5 L of ion exchange water for 5 hours. One hundred grams of the washed quartz sand was put into a vacuum flask. An aqueous sodium hydroxide solution (5.1 mL) with a concentration of $9.8\times10^{-5}$ mol/L was added thereto for mixing, and then the mixture was vacuum-dried over a hot water bath of 353 K till the water content (%: weight of water/weight of quartz sand×100) became 0%.

Subsequently, 5 mL of an aqueous potassium permanganate solution with a concentration of 0.7 g/L and 0.5 mL of silica sol (manufactured by Catalysts & Chemicals Industries, Co., Ltd.; Cataloid SA, trade name) were added thereto to mix fully, and the mixture was vacuum-dried till the water content became 0% over a hot water bath of 353 K. According to this technique, various detecting agents with different amounts of depositioned potassium permanganate were prepared. The thus obtained DMS detecting agents are referred to as detecting agents of the example. The above detecting agents are detecting agents with potassium permanganate deposited on quartz sand using silica sol and other detecting agents were prepared same method as in the above except that only potassium permanganate was deposited on quartz sand. The thus obtained DMS detecting agents are referred to as detecting agents of the comparative example.

<Preparation of Protectants>

Active alumina (manufactured by Fuji Davison Co., Ltd.; 40 to 60 meshes; specific surface area: 150 $m^2/g$; pore volume: 0.54 mL/g) was prepared, and 100 g thereof was put into a vacuum flask. 70 mL of an aqueous potassium permanganate solution with a concentration of 14.3 g/L was added thereto to mix fully, and then the mixture was vacuum-dried over a hot water bath with a temperature of 373 K for 3 hours. Subsequently, pure water was added to the dried product so that the water content was 14%.

The outline of the constitution of the thus prepared DMS detecting agent tube is as shown in FIG. 1. This tube is a glass tube with an inner diameter of 2.6 mm, and other dimensions are the same as shown in FIG. 1. The glass tube was charged with one glass bead 2 with a diameter of about 2 mm, an isolating agent 3 (0.25 g of molten alumina obtained by washing alumina with an aquenous sodium hydroxide solution, washing it with ion exchange water and vacuum-drying it), 0.35 g of the above-prepared detecting agent, an isolating agent 4 (0.10 g of the same molten alumina as the isolating agent 3), 0.04 g of a protectant and a polyethylene filler 7 (packing, 3 mm) in order and provided, and both ends of the glass tube were fused to prepare a DMS detecting agent tube.

(TBM Detector Tube: corresponding to a pretreatment tube in the case of the present example)

A t-butyl mercaptan (TBM) detector tube manufactured by Gastec Go., (catalogue No. 75L; range of measurement: 0.5 to 30 $mg/m^3$) was used. This has the constitution shown in FIG. 2 (glass tube; inner diameter: 2.6 mm), mercuric chloride and cresol red are used as a detecting agent (remover), and TBM is adsorbed thereto and removed. The thus prepared pretreatment tube and the above detecting agent tube were connected through a rubber tube 16 as shown in FIG. 3.

(Test 1: Test by the DMS Detecting Agent Tube and the DMS Detector Tube)

Figure 5:
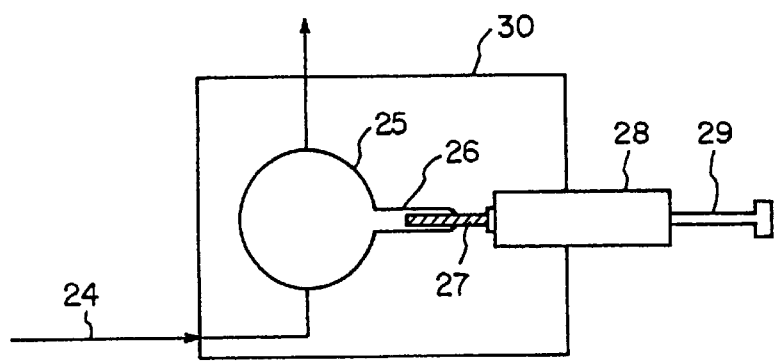
FIG. 5 is an experimental apparatus.

It is necessary to send a prescribed amount of a sample gas into the above-prepared DMS detecting agent tube or DMS detector tube, and FIG. 5 shows a device including a gas-collecting device for this. Here in FIG. 5, a detector tube 27 may be a DMS detecting agent tube alone or a DMS detector tube [TMB detector tube (=pretreatment tube)+ DMS detecting agent tube]; the description of a rubber tube connecting both required in the latter case is omitted. This device comprises a glass vessel 25 (about 500 ml) with a sample gas-collecting opening 26 provided thereon, and, first of all, the sample gas is taken into the vessel 25 from a gas tube 24.

Subsequently, the sample gas is introduced into the DMS detecting agent tube or the DMS detecting agent tube through the pretreatment tube by introducing the opening tip of the detector tube 27 into the sample gas-collecting opening 26 and sucking the sample gas in the vessel 25 by a vacuum-type gas-collecting device 28 connected to the side end part of the detector tube 27. 29 shows an operation rod for this. In this case, it is intended that a prescribed amount of the sample gas should reach the inside of the DMS detecting agent tube and in the present test, a vacuum-type gas-collecting device 28 with a suction volume of 100 ml was used. They were stored in a thermostat 30 for maintaining a constant temperature as shown in the drawing.

A sample gas to pass through the gas tube 241 was prepared by means of a permeater calibration gas-adjusting device (manufactured by Gastec Co.; PB•1B model). As a dilute gas was used clean dry air or dry air containing 2.5 vol ppm of TBM, and the flow rate was changed properly within the range of from 103 to 2506 mL/min. The sample gas used in examining the influence of humidity to be described later was prepared by separating a part of the dilute gas to moisten it and mixing it with the outlet gas of the permeater caribration gas-adjusting device.

A gas having a composition of 0.03% (vol %; hereunder, same as above) of $N_2$, 88.03% of $CH_4$, 5.39 % of $C_2H_6$, 5.02% of $C_3H_8$, 0.72% of i-$C_4H_{10}$, 0.79% of n-$C_4H_{10}$ and 0.02% of i-$C_5H_{12}$ was introduced into a Tedler back with a capacity of 5 L, and DMS alone or both TBM and DMS were added thereto to a city gas odorant concentration level to prepare a sample gas.

As standard reagents of TBM and DMS were used products manufactured by Tokyo Kasei Co., Ltd.

The DMS concentration (C) of the sample gas was obtained according to the following formula (1). In the formua, Pr denotes a gas permeation rate ($117.8\times10^{-6}$ mL/min-cm), L denotes a tube effective length (10 cm), and F denotes a dilute gas flow (from 103 to 2506 mL/min).

$$C(\text{vol ppm}) = \frac{Pr \times L \times 10^6}{F} \quad (1)$$

Figure 7:
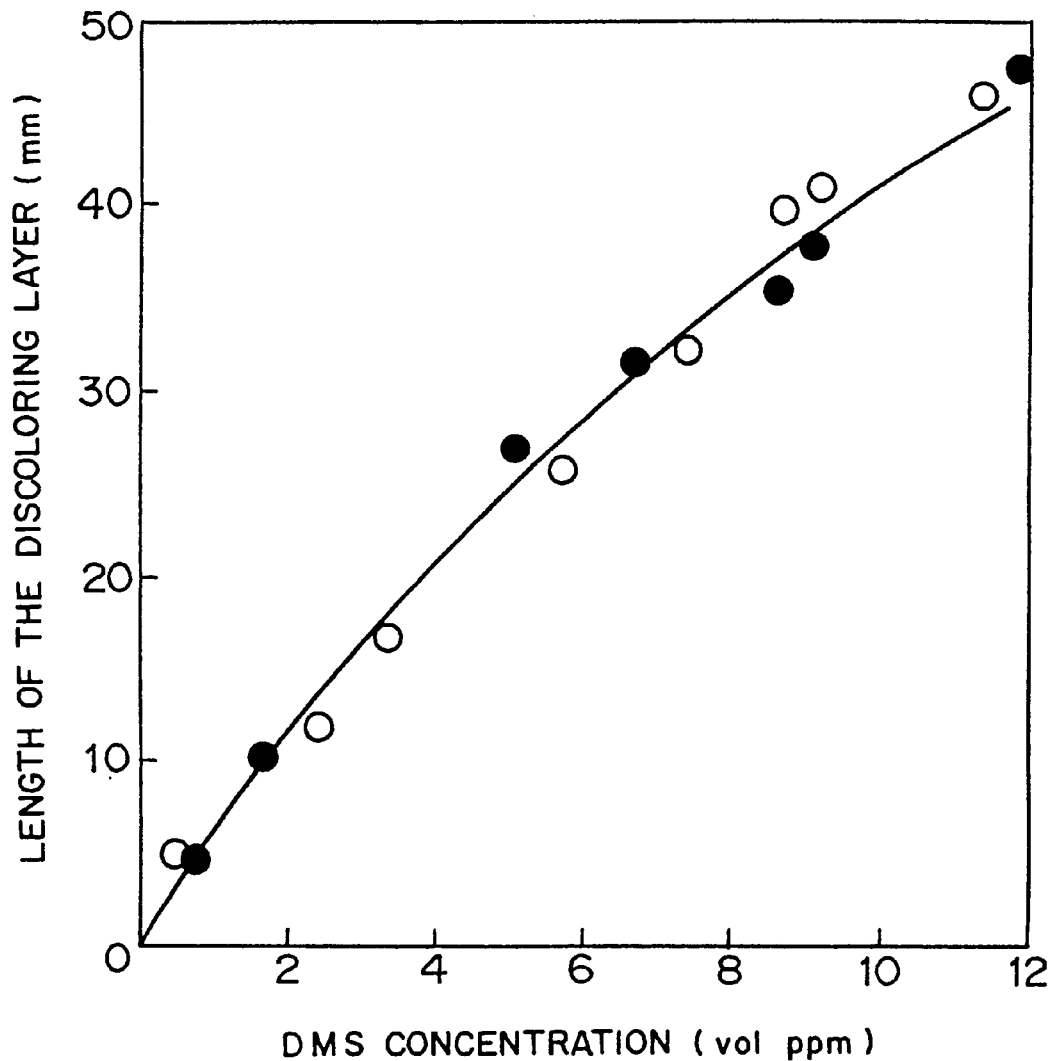
FIG. 7 is a diagram showing the length of a discoloring layer to the DMS concentration in the DMS detecting agent tube of the present invention.

FIG. 7 is a diagram showing the length of a discoloring layer to the DMS concentration obtained by the above test. In FIG. 7 are shown the case of the sample gas wherein a DMS detector tube was used and only DMS was added, changing the concentration thereof (in FIG. 7, marked with ●) and the case of the sample gas wherein TBM was 2.5 vol ppm and the DMS concentration was changed (in FIG. 7, marked with ○). Measurement was repeated for five runs (five DMS detector tubes were used), and an average measurement value obtained according to each measurement was made along the length of the discoloring layer. Since the measurement was conducted at room temperature (298 K), a temperature correction was performed to obtain a measurement value at 293 K.

As shown in FIG. 7, in the case of the sample gas containing only DMS as a sulfur compound, the length of the discoloring layer in the DMS detector tube [TBM detector tube+DMS detecting agent tube] was measured in accordance with the DMS concentration, and an excellent correlation is shown.

The same results were obtained in the case of using a DMS detecting agent tube (only DMS detecting agent tube not using a pretreatment tube). In the case of the sample gas with DMS added therein to TBM of 2.5 vol ppm, the length of the discoloring layer was measured in accordance with the DMS concentration, and both show an excellent correlation. Thus, no influence of TBM on the length of the discoloring layer of the DMS detecting agent tube was observed in the case that two kinds of detector tubes were connected so that the sample gas should pass through the TBM detector tube (pretreatment tube) and the DMS detecting agent tube in order.

(Test 2: Test of the Influence of Temperature upon the Length of the Discoloring Layer of the DMS Detecting Agent Tube)

Figure 8:
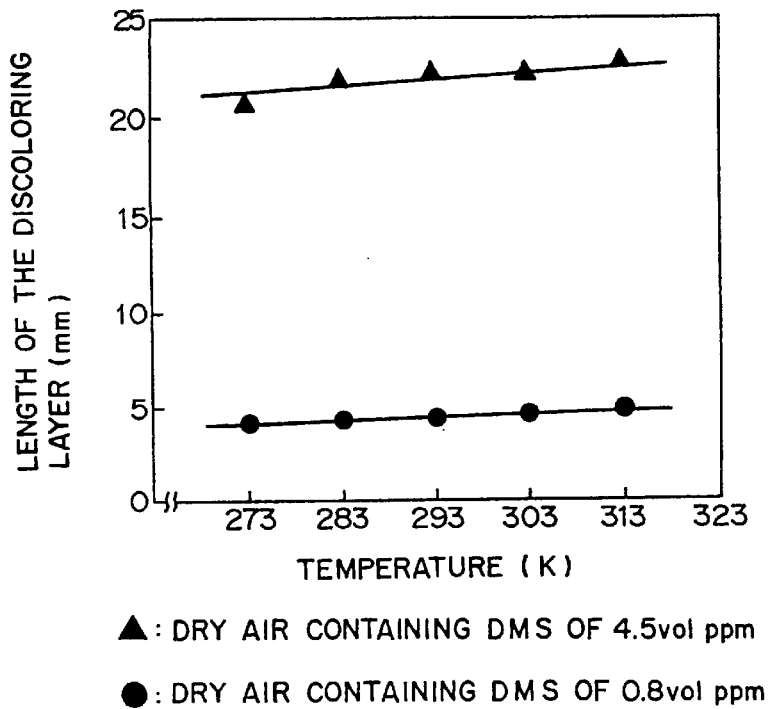
FIG. 8 is a diagram showing the influence of measurement temperature upon the length of a discoloring layer in the DMS detecting agent tube of the present invention.

FIG. 8 shows the results of examining the influence of temperature upon the length of the discoloring layer according to the same technique as in Test 1.

Figure 9:
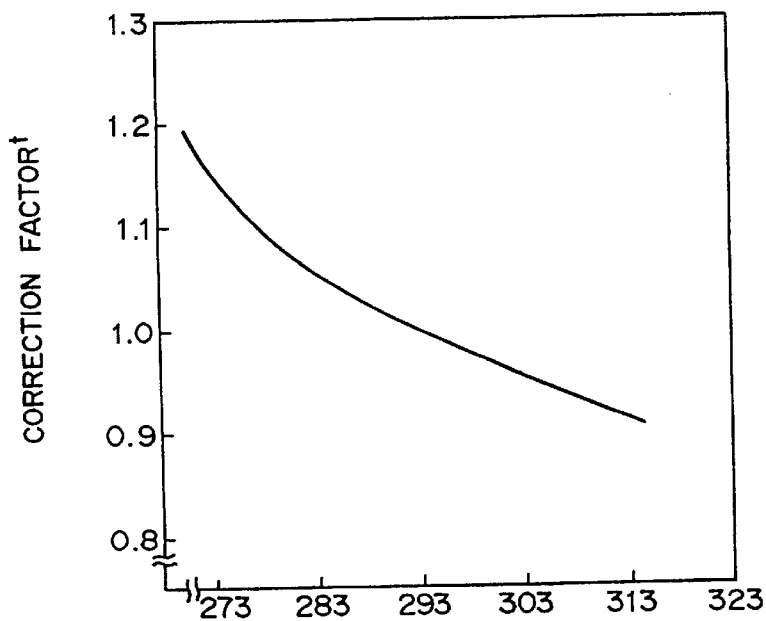
FIG. 9 is a diagram showing the temperature correction curve employed in Test 2 (test of FIG. 8).

FIG. 9 shows a temperature correction curve in this case. As is shown in FIG. 8, it has been revealed that the length of the discoloring layer lengthens slightly according to the rise in measurement temperature. This shows that the DMS detecting agent tube and the DMS detector tube of the present invention can be used effectively at normal temperature or an ordinary environment temperature.

(Test 3: Test of the Influence of Humidity upon the Length of the Discoloring Layer of the DMS Detecting Agent Tube)

The water content of city gas with LNG as a main raw material is of the order of 10 vol ppm. This water content corresponds to 0.043% of relative humidity.

Hence, regarding two kinds of sample gases with different DMS concentrations, measurements were conducted on those moistened to 10% and those non-moistened and measurement values were compared. As a result, no change of length of the discoloring layer was observed on those moistened. It has been proved as a result that the influence of water content in a gas can be disregarded.

(Test 4: Test of the Precision of the Measurement of the DMS Detecting Agent Tube)

A gas chromatograph equipped with a flame photometric detector (FPD-GC method) is an excellent technique for measuring the amount of an odorant at a laboratory level. The present Test 4 tested the precision of the measurement of the DMS detecting agent tube of the present invention according to a comparison with the results by the FPD-GC method. As a result, regarding the sample gases with the same DMS concentration, a value of 3.7 mg/m$^3$ was obtained according to the FPD-GC method, while a value of 3.8 mg/m$^3$ was obtained according to the DMS detecting agent tube of the present invention. Moreover, regarding five runs repetition precision, a relative standard deviation of 4.5% was obtained according to the FPD-GC method, while a relative standard deviation of 5.1% was obtained according to the DMS detecting agent tube of the present invention. Thus, it has been revealed that the DMS detecting agent tube of the present invention is excellent in the precision of measurement.

(Test 5: Test of the Evaluation of Stability)

In the present Test 5, the prepared DMS detecting agent tubes were stored in a constant temperature room of 288 K and not exposed to the direct sunlight for about 120 days. During the term of storage, five detector tubes were taken out at an interval of several days, and the same measurement as in the above Test 1 was conducted using them. As a result, the same values of measurement as those obtained immediately after the preparation were obtained, even after 120 days. On the other hand, under the direct sunlight, the whole detecting agent layer discolored to white in about one hour. Hence, it has been revealed that the performance of the DMS detecting agent tube of the present invention can be maintained for a long period of time by storing it at a temperature below room temperature avoiding the direct sunlight.

According to the DMS detecting agent of the present invention, the presence and amount of DMS contained as an odorant in a fuel gas such as city gas and LP gas or generated at a manufacturing factory and life environment can be measured rapidly and at a high precision. In addition, a DMS detecting agent tube and a DMS detector tube comprising the detecting agent of the present invention have excellent performances such as simplicity, rapidness, a high precision and an extremely small readout error.

What is claimed is:

1. A DMS detecting agent comprising a permanganate and a silica sol or alumina sol deposited on a support, said support being quartz sand and the DMS detecting agent being obtained by adding an aqueous solution of silica sol or alumina sol and a permanganate to said quartz sand support to form a mixture and then drying the mixture.

2. A DMS detecting agent as claimed in claim 1, wherein said permanganate is potassium permanganate.

3. A DMS detecting agent as claimed in claim 1, wherein said DMS detecting agent is used for detecting DMS in a fuel gas or detecting DMS generated at a manufacturing factory or life environment.

4. A DMS detecting agent as claimed in claim 3, wherein said fuel gas is city gas or LP gas.

5. A process for preparing a DMS detecting agent with a permanganate deposited on a support, comprising using quartz sand as a support, washing said quartz sand support with pure water, adding an aqueous solution of silica sol or alumina sol and a permanganate thereto to form a mixture and drying the mixture.

6. A process for preparing a DMS detecting agent as claimed in claim 5, wherein said drying is performed by vacuum drying.

7. A DMS detecting agent tube, characterized in that said DMS detecting agent tube is charged with a DMS detecting agent obtained by adding an aqueous solution of silica sol or alumina sol and a permanganate to a quartz sand support to form a mixture and then drying the mixture.

8. A detector tube for DMS in a fuel gas comprising a pretreatment tube and a DMS detecting agent tube, characterized in that said DMS detecting agent tube is a DMS detecting agent tube charged with a DMS detecting agent obtained by adding an aqueous solution of silica sol or alumina sol and a permanganate to a quartz sand support to mix and then drying the mixture.

* * * * *